United States Patent [19]
Cicio

[11] Patent Number: 5,408,703
[45] Date of Patent: Apr. 25, 1995

[54] FEMALE URINATION AID

[76] Inventor: William Cicio, 89 Broadway, Massapequa Park, N.Y. 11762

[21] Appl. No.: 69,699

[22] Filed: Jun. 1, 1993

Related U.S. Application Data

[63] Continuation-in-part of Ser. No. 807,703, Dec. 16, 1991, abandoned.

[51] Int. Cl.6 ............................................. A47K 11/12
[52] U.S. Cl. .................................... 4/144.2; 4/144.4
[58] Field of Search ............................ 4/144.1–144.4

[56] References Cited

U.S. PATENT DOCUMENTS

| | | |
|---|---|---|
| 1,510,973 | 10/1924 | Behan . |
| 2,878,486 | 3/1959 | Bartlett et al. ............... 4/144.4 |
| 3,306,515 | 2/1967 | Beaumont ..................... 229/22 |
| 3,558,102 | 1/1971 | Davis . |
| 3,864,759 | 2/1975 | Horiuchi . |
| 3,964,111 | 6/1976 | Packer . |
| 3,995,329 | 12/1976 | Williams . |
| 4,023,216 | 5/1977 | Li . |
| 4,296,502 | 10/1981 | Bortle ............................ 4/114.1 |
| 4,528,703 | 7/1985 | Kraus ............................ 4/144.2 |
| 4,608,046 | 8/1986 | Towfigh ..................... 4/144.3 X |
| 4,626,249 | 12/1986 | Hamey ........................... 604/329 |
| 4,681,573 | 7/1987 | McGovern et al. ......... 4/144.3 X |
| 4,751,751 | 6/1988 | Reno .............................. 4/144.4 |
| 4,937,890 | 7/1990 | Tafur ............................. 4/144.4 |

FOREIGN PATENT DOCUMENTS

| | | |
|---|---|---|
| 158602 | 10/1985 | European Pat. Off. . |
| 0002943 | 2/1894 | United Kingdom ............ 4/144.3 |
| 2323597 | 12/1990 | United Kingdom . |
| WO82/02831 | 9/1982 | WIPO . |

Primary Examiner—Charles E. Phillips
Attorney, Agent, or Firm—Standley & Gilcrest

[57] ABSTRACT

A disposable device for assisting a female in urinating from a standing position and for directing the urine a suitable distance away from the female, the device including a first end having a contoured opening for receiving urine from a female, a second end having an opening for discharging the urine from the device and first and second longitudinal creases extending from the first end to the second end and defining first and second walls.

7 Claims, 3 Drawing Sheets

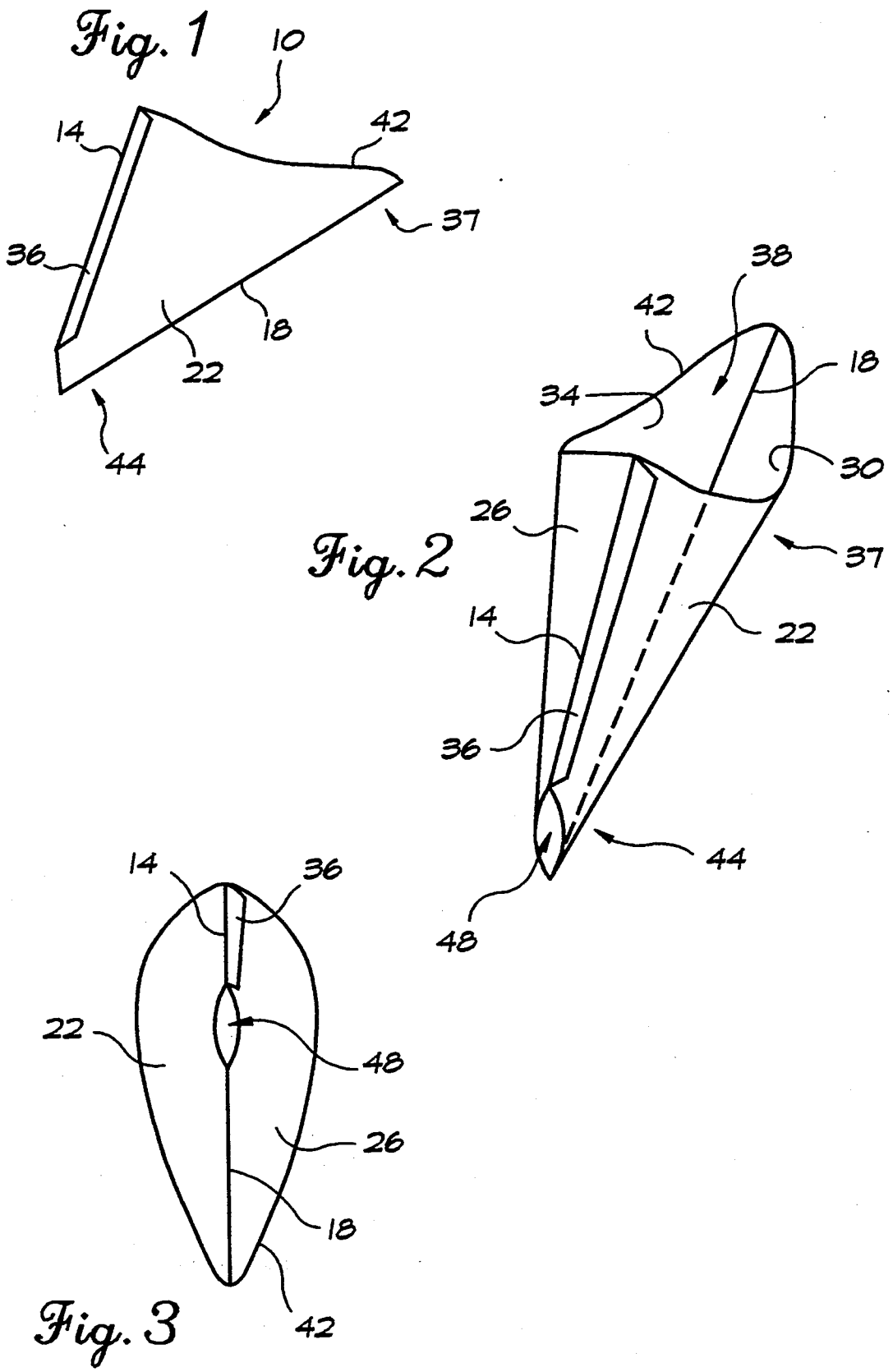

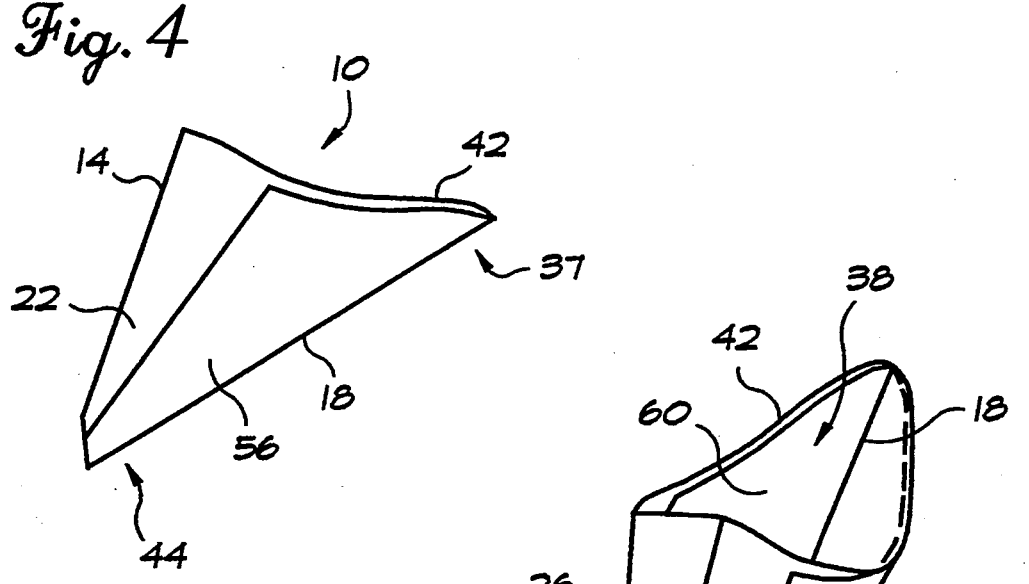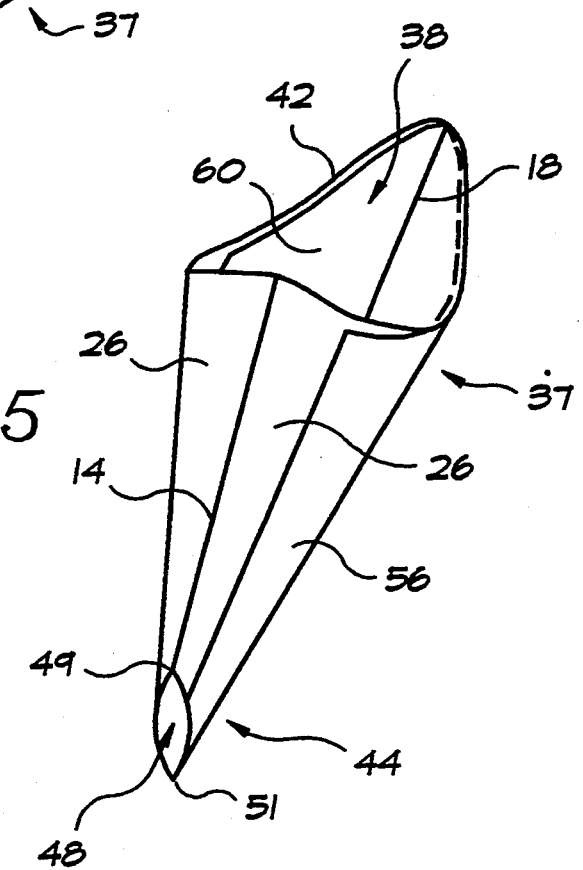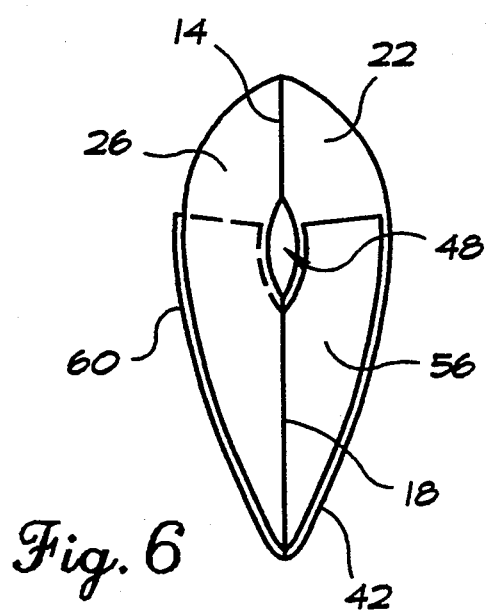

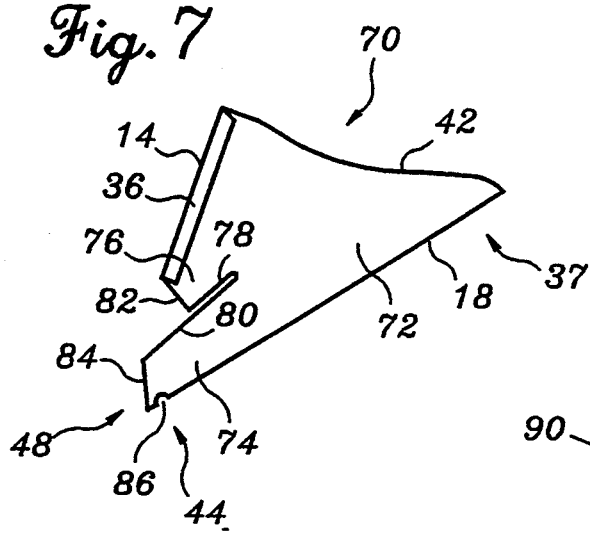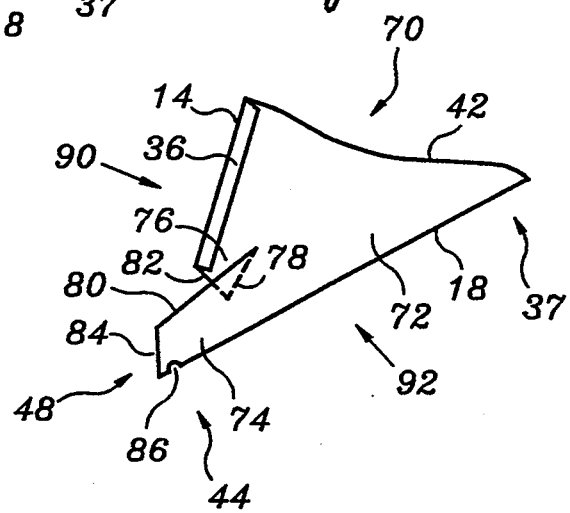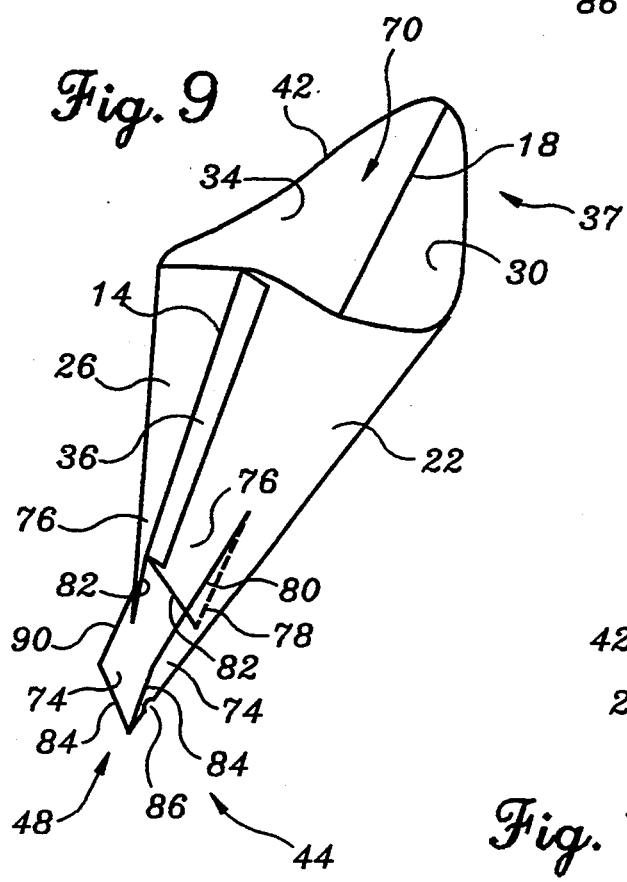

FEMALE URINATION AID

This is a continuation-in-part of application Ser. No. 07/807,703, filed Dec. 16, 1991 now abandoned.

BACKGROUND OF THE INVENTION

This invention relates to female urination devices, and more particularly, to devices which allow a female to urinate from a standing position.

Public restrooms for women are very often unclean and unsanitary. The toilet seats in public restrooms are often dirty or otherwise in an unsanitary condition. Because of this, women do not want to touch the toilet seat, and therefore, they often squat above the toilet seat when using the restroom. This is a very difficult and unpleasant way for a woman to urinate. Likewise, when camping or traveling, a woman's restroom may not be available and a woman may have to squat while holding her clothing out of the way in order to urinate.

Attempts have been made to design a urination device which will assist a woman in urinating from a standing position. However, many of these devices are complicated and cumbersome to use.

SUMMARY OF THE INVENTION

The present invention provides a unique disposable device for assisting a female in urinating from a standing position and for directing the urine a suitable distance away from the female, the device comprising a first end having an opening for receiving urine from a female, the opening having a circumference which is contoured to fit around the outside of the female's vulva, a second end opposite the first end and having an opening for discharging the urine from the device and a longitudinal crease extending from the first end to the second end.

The invention also provides a disposable device for assisting a female in urinating from a standing position and for directing the urine a suitable distance away from the female, the device comprising a first end having an opening for receiving urine from a female, a second end having an opening for discharging the urine from the device, the opening in the second end having a top surface and a bottom surface wherein the bottom surface extends beyond the top surface to create an angled opening and first and second longitudinal creases extending from the first end to the second end.

The invention also provides a disposable device for assisting a female in urinating from a standing position and for directing the urine a suitable distance away from the female, the device comprising a first end having an opening for receiving urine from a female, a second end having an opening for discharging the urine from the device and first and second longitudinal creases extending from the first end to the second end, the creases defining first and second walls each having an inside surface wherein the inside surface is coated with a moisture-resistant coating. The device may be split at its second end to comprise a lower v-shaped trough and an upper, inverted v-shaped guide. The upper, inverted v-shaped guide is preferably significantly shorter in length than the lower trough, and acts as a guide to control fluid turbulence. A hole may be added at or near the end of the lower trough as a braking mechanism against drips.

It is an object of the present invention to provide a female urination device which allows a woman to urinate from a standing position and which is inexpensive and simple to use.

It is another object of the invention to provide a female urination device which allows a woman to urinate from a standing position and which may be stored in a folded condition and disposed of after use.

A further object of the invention is to provide a female urination device to assist a female in urinating from a standing position which is contoured to fit around a woman's vulva.

Other principal features and advantages of the invention will become apparent to those skilled in the art upon review of the following detailed description, claims and drawings.

BRIEF DESCRIPTION OF THE DRAWINGS

FIG. 1 is a side view of the device in a closed or flat configuration;

FIG. 2 is an isometric view of the device in an open or usable configuration;

FIG. 3 is an end view of the device in an open or usable configuration;

FIG. 4 is a side view of an alternative embodiment of the device in a closed or flat configuration;

FIG. 5 is an isometric view of the device of FIG. 4 in an open or usable configuration;

FIG. 6 is an end view of the device illustrated in FIG. 5,

FIG. 7 is a side view of another embodiment of the present invention in a closed configuration;

FIG. 8 is a side view of the device of FIG. 7 in an open configuration;

FIG. 9 is a perspective view of the device of FIG. 8; and

FIG. 10 is an end view of the device of FIG. 9.

Before one embodiment of the invention is explained in detail, it is to be understood that the invention is not limited in its application to the details of construction and the arrangement of components set forth in the following description or illustrated in the drawings. The invention is capable of other embodiments and of being practiced or carried out in various ways. Also, it should be understood that the phraseology and terminology used herein is for the purpose of description and should not be regarded as limiting.

DESCRIPTION OF THE PREFERRED EMBODIMENTS

A female urination device 10 embodying the invention is illustrated in the drawings.

The device 10 includes a first or upper longitudinal crease 14 and a second or lower longitudinal crease 18. These creases 14 and 18 define first and second walls 22 and 26. These walls 22 and 26 may be made of any suitable water-absorbant paper or cardboard. These walls 22 and 26 further have inside surfaces 30 and 34 respectively which may be coated with a thin, moisture-resistant coating which prevents the urine passing through the device 10 from effecting its structural integrity. One of the walls 22 includes a tab 36 that is glued or otherwise attached to the opposite wall 26 with a water soluble glue or the like.

The device 10 is preferably stored in a flattened manner as illustrated in FIG. 1 such as would be the case if the device was stored in a package, dispensing machine or the like. In order to get the device to an open or usable configuration, all that is required is that pressure be applied to the two creases 14 and 18, such as by the thumb and the index finger, to push the creases 14 and 18 toward one another. This open or usable configuration is illustrated in FIG. 2.

The device 10 has a first end 37 having a first or larger opening 38. Once the device 10 has been opened, the device can be used by placing the first or larger opening 38 around the outside of the woman's vulva. It should be noticed that this first or larger opening 38 has a circumference 42 which is contoured to insure a tight fit around the vulva when the device is held in place during use. This contour could be described as a "shallow cosinal curvature" when viewed from either side when the device is in a flattened position. This contour or curvature of the first or larger opening 38 also provides more comfort than would be the case if the end merely had a U-shaped curvature, as the U-shaped curvature would result in a point at the front and rear of the opening.

With the larger or first opening 38 placed around the outside of the woman's vulva, the woman may urinate from a standing position. The device is preferably placed around the vulva such that the lower longitudinal crease 18 is at the bottom of the device so that the bottom longitudinal crease 18 can serve as a trough which will focus the urine into a stream form.

The urine will travel down the device to the second end 44 and exit the device through the discharge opening 48. Although the discharge opening 48 may be of any suitable form, the discharge opening 48 is preferably angled such that the bottom or lower longitudinal crease 18 extends beyond the upper longitudinal crease 14. In other words, the discharge opening has a top surface and a bottom surface and the bottom surface extends beyond the top surface such that the angle created by an imaginary line extending from the most forward edge 49 of the upper longitudinal crease 14 to the most forward edge 51 of the lower longitudinal crease 18, with respect to the lower longitudinal crease 18, is less than 90° and preferably is between 35° and 85°. This angled discharge opening prevents urine from "dribbling" out of the opening 48 and provides for a clean discharge of the urine a suitable distance away from the female and from the device.

Since this device may be constructed of water-absorbant paper and may be held together with a water soluble glue, the device can be disposed of by being flushed down a toilet as the device will quickly soften once it touches the water. The water-soluble glue allows the device to disassemble in water, further reducing its structural integrity.

An alternative embodiment of the invention is illustrated in FIGS. 4–6. This alternative embodiment operates in the same manner as the previously discussed device illustrated in FIGS. 1–3 and like elements will be given like reference numbers.

The device illustrated in FIGS. 4–6 has a first end 37 having a first or larger opening 38 for receiving urine from a female. This first opening has a circumference 42 which is contoured to fit around the outside of a female's vulva. This circumference 42 can be described as having a "shallow cosinal curvature" when viewed from the side as illustrated in FIG. 4.

The device also has a second or dicharge end 44 opposite the first opening 38 and having an opening 48 for discharging the urine from the device.

The device further includes a first lower longitudinal crease 18 and a second upper longitudinal crease 14 which define first and second walls 22 and 26. Each of these walls 22 and 26 have respective overlap tabs 56 and 60 for sealing the device. These tabs 56 and 60 overlap one another and may be sealed with a water-resistant glue, such as but not limited to rubber cement. In this embodiment, it is no longer necessary to coat the inside surface of the walls with a water-resistant coating. This is because the tabs 56 and 60 are sealed to the walls 22 and 26 using a rubber cement. The water-resistant glue that is sandwiched between the tabs 56 and 60 and the walls 22 and 26 will prevent leak-through of the urine along the lower crease 18. In this regard, it is preferable to make the tabs 56 and 60 wide enough so that they preferably extend approximately two-thirds of the way up the walls 22 and 26. However, the tabs 56 and 60 could extend to completely overlap walls 22 and 26 or below two-thirds of the way up the walls 22 and 26.

This device operates in the same manner as the previously described embodiment. The first opening 38 is placed around the woman's vulva and the woman can urinate into the device and the urine will exit through the second or discharge opening 48. The second or discharge opening 48 in this embodiment is likewise preferably angled as previously described so as to prevent urine from dribbling out of the discharge opening 48 and allowing the urine to cleanly exit the device.

With reference to FIGS. 7–10, another embodiment of the present invention is shown generally at reference numeral 70. This alternative embodiment operates in a similar manner as the previously discussed devices illustrated in FIGS. 1–6 and like elements will be given like reference numbers.

The present embodiment illustrated in FIGS. 7–10 establishes three uniquely different regions of the device, the main body 72, the lower v-shaped trough 74, and the upper inverted v-shaped guide 76. The lower longitudinal crease 18 not only establishes the bottom edge of the body of the device, but it also establishes the bottom edge of the lower v-shaped trough 74. Conversely, the corresponding upper longitudinal crease 14 not only establishes the top edge of the body of the device, but it also establishes the top edge of the upper inverted v-shaped guide 76.

As the device 70 is squeezed to open by applying opposing forces simultaneously at the upper and lower longitudinal creases in directions 90 and 92, the upper longitudinal crease 14 angles downward toward the lower longitudinal crease 18, and the upper inverted v-shaped guide 76 moves downward into the lower v-shaped trough 74 where it acts as a buffer against fluid turbulence. The overlapping flap or tab 36 does not extend along a distance equal to the length of the device, but instead is truncated along with the inverted upper v-shaped guide 76. The rigidity of this shortened overlap 36 in this embodiment aids in forcing the inverted upper v-shaped guide 76 to descend into the lower v-shaped trough 74 when the device 70 is squeezed open.

As the device 70 is squeezed open, the two descending flanks 78 formed from a slit in each of the walls 22 and 26 move downward inside the two Upper edges 80 defining the lower trough. The two leading edges of the upper guide 82 and the two leading edges of the lower trough 84 form the discharge opening 48.

A small hole 86 may be added at or near the end of the lower trough, preferably in the lower longitudinal crease, as a braking mechanism against drips.

After use, the device can be disposed of either by throwing it in the trash or by throwing it in the toilet since the device is water absorbant.

Various features of the invention are set forth in the following claims.

What is claimed is:

1. A disposable device for assisting a female in urinating from a standing position and for directing the urine a suitable distance away from the female, said device comprising;
    a first end having an opening for receiving urine from a female;
    a second end having an opening for discharging the urine from said device;
    an upper longitudinal crease extending from said first end to said second end;
    a lower longitudinal crease extending from said first end to said second end, such that said upper and lower creases define first and second walls;
    an upper inverted V-shaped guide, defined by said upper longitudinal crease and a slit in each of said first and second walls; and
    a lower V-shaped trough, defined by said lower longitudinal crease and said slits.

2. The device of claim 1 wherein said opening in said second end has a top surface and a bottom surface and wherein said bottom surface extends beyond said top surface to create an angled opening in said second end.

3. A disposable device for assisting a female in urinating from a standing position and for directing the urine a suitable distance away from the female, said device comprising:
    a first end having an opening for receiving urine from a female;
    a second end having an opening for discharging the urine from said device;
    an upper longitudinal crease extending from said first end to a point significantly short of said second end;
    a lower longitudinal crease extending from said first end to said second end, such that said upper and lower creases define first and second walls;
    an upper inverted V-shaped guide, defined by said upper longitudinal crease and a slit in each of said first and second walls; an
    a lower V-shaped trough, defined by said lower longitudinal crease and said slits.

4. The device of claim 3 wherein said opening in said first end has a circumference which is contoured in a cosinal curvature configuration to fit around the outside of the female's vulva.

5. The device of claim 3 wherein one of said first and second walls includes a tab which extends across the other of said first and second walls to close and seal said device.

6. The device of claim 3, further comprising: means for breaking flow through said device to inhibit dripping from said second end.

7. The device of claim 6, wherein said means for breaking flow is a small hole located in said lower longitudinal crease, near said second end, to capture any final drips.

* * * * *